(12) United States Patent
Tezel et al.

(10) Patent No.: US 11,992,668 B2
(45) Date of Patent: May 28, 2024

(54) INJECTION DEVICE

(71) Applicant: Allergan, Inc., Irvine, CA (US)

(72) Inventors: Ahmet Tezel, Fort Worth, TX (US); Kevin McNerney, Huntington Beach, CA (US); Christopher S. Mudd, Lake Forest, CA (US); Blake R. Storie, Laguna Niguel, CA (US); Bastien Mandaroux, Cran Gevrier (FR)

(73) Assignee: Allergan, Inc., Irvine, CA (US)

( * ) Notice: Subject to any disclaimer, the term of this patent is extended or adjusted under 35 U.S.C. 154(b) by 1139 days.

(21) Appl. No.: 16/358,553

(22) Filed: Mar. 19, 2019

(65) Prior Publication Data
US 2019/0209789 A1    Jul. 11, 2019

Related U.S. Application Data

(63) Continuation of application No. 12/629,480, filed on Dec. 2, 2009, now Pat. No. 10,232,129.

(60) Provisional application No. 61/139,430, filed on Dec. 19, 2008, provisional application No. 61/119,298, filed on Dec. 2, 2008.

(51) Int. Cl.
*A61M 5/34* (2006.01)
*A61M 5/32* (2006.01)

(52) U.S. Cl.
CPC ........... *A61M 5/347* (2013.01); *A61M 5/3293* (2013.01); *A61M 2210/04* (2013.01)

(58) Field of Classification Search
CPC ............................ A61M 5/347; A61M 5/3293
See application file for complete search history.

(56) References Cited

U.S. PATENT DOCUMENTS

| | | | |
|---|---|---|---|
| 1,250,114 A | 12/1917 | Bigelow et al. |
| 1,558,037 A | 10/1925 | Morton |
| 1,591,021 A | 7/1926 | Davis |
| 2,007,140 A | 7/1935 | Ragnar |
| 2,302,986 A | 11/1942 | Vollrath |
| 2,491,978 A | 12/1949 | Helfman |

(Continued)

FOREIGN PATENT DOCUMENTS

| | | |
|---|---|---|
| CN | 2088857 | 11/1991 |
| CN | 2535071 | 2/2003 |

(Continued)

OTHER PUBLICATIONS

Notice of Opposition from European Patent Application No. 17155371. 2, dated Jan. 27, 2021, 58 pages.

(Continued)

*Primary Examiner* — Ariana Zimbouski
*Assistant Examiner* — John A Doubrava
(74) *Attorney, Agent, or Firm* — Mintz, Levin, Cohn, Ferris, Glovsky and Popeo, P.C.

(57) ABSTRACT

A needle assembly for an injection device is provided to facilitate delivery of a dermal filler. The assembly includes a cannula and a hub. The hub can be coupled to a syringe. The hub includes an inner bore that has a proximal retention section, a stepped section, and a cannula retention section. The stepped section, the proximal retention section, and the cannula retention section are configured to reduce the dead space within the inner bore for preventing detachment of the hub from the syringe during an injection procedure.

16 Claims, 2 Drawing Sheets

(56) References Cited

U.S. PATENT DOCUMENTS

| | | | |
|---|---|---|---|
| 2,551,902 A | 5/1951 | Rieck | |
| 2,737,946 A | 3/1956 | Hein, Jr. | |
| 2,853,070 A | 9/1958 | Julliard | |
| 3,086,530 A | 4/1963 | Groom | |
| 3,161,323 A | 12/1964 | Bent | |
| D202,754 S | 11/1965 | Fnftolin | |
| D214,112 S | 5/1969 | Langdon | |
| 3,517,668 A | 6/1970 | Brickson | |
| 3,595,231 A | 7/1971 | Pistor | |
| D224,066 S | 6/1972 | McDonald | |
| 3,720,211 A | 3/1973 | Kyrias | |
| 3,767,085 A | 10/1973 | Cannon et al. | |
| 3,807,048 A | 4/1974 | Malmin | |
| 3,910,282 A | 10/1975 | Messer et al. | |
| 3,916,777 A | 11/1975 | Earl | |
| 3,941,128 A * | 3/1976 | Baldwin | A61M 5/286 604/199 |
| 4,064,879 A | 12/1977 | Leibinsohn | |
| 4,240,423 A | 12/1980 | Akhavi | |
| 4,240,426 A | 12/1980 | Akhavi | |
| 4,273,122 A | 6/1981 | Whitney et al. | |
| 4,326,517 A | 4/1982 | Whitney et al. | |
| 4,346,708 A | 8/1982 | Leeven | |
| 4,444,560 A | 4/1984 | Jacklich | |
| 4,529,401 A | 7/1985 | Leslie et al. | |
| 4,617,016 A | 10/1986 | Blomberg | |
| 4,624,659 A | 11/1986 | Goldberg | |
| 4,671,255 A | 6/1987 | Dubrul et al. | |
| 4,695,273 A | 9/1987 | Brown | |
| 4,699,612 A | 10/1987 | Hamacher | |
| 4,710,172 A | 12/1987 | Jacklich | |
| 4,719,918 A | 1/1988 | Bonomo et al. | |
| 4,755,169 A | 7/1988 | Sarnoff | |
| 4,759,750 A | 7/1988 | Devries | |
| 4,800,901 A | 1/1989 | Rosenberg | |
| 4,832,692 A | 5/1989 | Box | |
| 4,841,948 A | 6/1989 | Bauser et al. | |
| 4,841,992 A | 6/1989 | Sasaki et al. | |
| 4,846,886 A | 7/1989 | Fey et al. | |
| D303,010 S | 8/1989 | Jabbusch | |
| 4,869,717 A | 9/1989 | Adair | |
| 4,908,029 A | 3/1990 | Bark et al. | |
| 4,955,905 A | 9/1990 | Reed | |
| 4,957,744 A | 9/1990 | dellaValle et al. | |
| 5,024,656 A | 6/1991 | Gasaway et al. | |
| 5,046,506 A | 9/1991 | Singer | |
| 5,066,303 A | 11/1991 | Bark et al. | |
| 5,092,348 A | 3/1992 | Dubrul et al. | |
| 5,100,390 A | 3/1992 | Lubeck et al. | |
| 5,104,375 A | 3/1992 | Lubeck et al. | |
| 5,116,358 A | 5/1992 | Granger et al. | |
| 5,127,436 A | 7/1992 | Campion et al. | |
| 5,141,496 A | 8/1992 | Dalto et al. | |
| 5,211,644 A | 5/1993 | VanBeek et al. | |
| 5,258,013 A | 11/1993 | Granger et al. | |
| 5,270,685 A | 12/1993 | Hagen | |
| 5,279,544 A | 1/1994 | Gross | |
| 5,295,980 A | 3/1994 | Ersek | |
| 5,305,788 A | 4/1994 | Mayeux | |
| 5,318,544 A | 6/1994 | Drypen | |
| 5,322,511 A | 6/1994 | Armbruster et al. | |
| 5,344,407 A | 9/1994 | Ryan | |
| 5,354,279 A | 10/1994 | Hofling | |
| 5,356,383 A | 10/1994 | Daly et al. | |
| 5,368,572 A | 11/1994 | Shirota | |
| 5,383,851 A | 1/1995 | Mackinnon, Jr. | |
| 5,405,330 A | 4/1995 | Zunitch et al. | |
| 5,433,352 A | 7/1995 | Ronvig | |
| 5,478,327 A | 12/1995 | McGregor et al. | |
| 5,489,272 A * | 2/1996 | Wirtz | A61M 5/322 604/110 |
| 5,540,657 A | 7/1996 | Kurjan | |
| 5,549,672 A | 8/1996 | Maddock et al. | |
| 5,611,809 A | 3/1997 | Marshall et al. | |
| D378,939 S | 4/1997 | Smith et al. | |
| 5,690,618 A | 11/1997 | Smith et al. | |
| 5,752,970 A | 5/1998 | Yoon | |
| 5,792,099 A | 8/1998 | Decamp et al. | |
| 5,807,340 A | 9/1998 | Pokras | |
| 5,817,033 A * | 10/1998 | DeSantis | A61B 10/0275 600/564 |
| 5,824,335 A | 10/1998 | Dorigatti et al. | |
| 5,846,225 A | 12/1998 | Rosengart et al. | |
| 5,941,845 A | 8/1999 | Tu et al. | |
| 5,951,528 A | 9/1999 | Parkin | |
| 5,964,737 A | 10/1999 | Caizza | |
| D424,194 S | 5/2000 | Holdaway et al. | |
| 6,077,251 A | 6/2000 | Ting et al. | |
| 6,102,929 A | 8/2000 | Conway et al. | |
| 6,159,233 A | 12/2000 | Matsuzawa | |
| 6,171,276 B1 | 1/2001 | Lippe | |
| 6,183,434 B1 | 2/2001 | Eppstein | |
| D441,077 S | 4/2001 | Garito et al. | |
| 6,231,552 B1 | 5/2001 | Jentzen | |
| 6,231,570 B1 | 5/2001 | Tu et al. | |
| 6,283,951 B1 | 9/2001 | Flaherty et al. | |
| 6,293,925 B1 | 9/2001 | Safabash et al. | |
| 6,303,518 B1 | 10/2001 | Aceti | |
| 6,312,412 B1 | 11/2001 | Saied | |
| 6,432,046 B1 | 8/2002 | Yarush et al. | |
| 6,451,240 B1 | 9/2002 | Sherman et al. | |
| 6,482,187 B1 | 11/2002 | Gibbs | |
| 6,488,651 B1 | 12/2002 | Morris | |
| 6,551,290 B1 | 4/2003 | Elsberry et al. | |
| 6,595,960 B2 | 7/2003 | West et al. | |
| 6,607,512 B2 | 8/2003 | Oliver | |
| 6,607,513 B1 | 8/2003 | Down | |
| 6,611,707 B1 | 8/2003 | Prausnitz et al. | |
| 6,613,010 B2 | 9/2003 | Castellano | |
| 6,616,448 B2 | 9/2003 | Friedman | |
| D483,116 S | 12/2003 | Castellano | |
| 6,689,095 B1 | 2/2004 | Garitano et al. | |
| 6,689,103 B1 | 2/2004 | Palasis | |
| 6,780,171 B2 | 8/2004 | Gabel | |
| 6,783,514 B2 | 8/2004 | Tovey et al. | |
| 6,824,526 B2 | 11/2004 | Castellano | |
| 6,896,666 B2 | 5/2005 | Kochamba | |
| 6,901,850 B2 | 6/2005 | Corominas | |
| 6,908,453 B2 | 6/2005 | Fleming | |
| 6,936,297 B2 | 8/2005 | Roby et al. | |
| 6,945,952 B2 | 9/2005 | Kwon | |
| 7,004,928 B2 | 2/2006 | Aceti | |
| 7,018,356 B2 | 3/2006 | Wise et al. | |
| 7,033,337 B2 | 4/2006 | Hjertman | |
| 7,041,088 B2 | 5/2006 | Nawrocki et al. | |
| 7,047,070 B2 | 5/2006 | Wilkinson et al. | |
| 7,048,729 B2 | 5/2006 | Meglin et al. | |
| 7,097,631 B2 | 8/2006 | Trautman | |
| 7,108,681 B2 | 9/2006 | Gartstein | |
| 7,115,108 B2 | 10/2006 | Wilkinson et al. | |
| 7,150,726 B2 | 12/2006 | Dalton | |
| 7,302,885 B2 | 12/2007 | Townsend | |
| 7,361,163 B2 | 4/2008 | Cohen | |
| 7,419,472 B2 | 9/2008 | Hibner et al. | |
| 7,442,187 B2 | 10/2008 | Khayal et al. | |
| 7,494,473 B2 | 2/2009 | Eggers et al. | |
| 7,504,386 B2 | 3/2009 | Pressato et al. | |
| 7,556,615 B2 | 7/2009 | Pettis et al. | |
| 7,559,952 B2 | 7/2009 | Pinchuk | |
| 7,588,547 B2 | 9/2009 | Deem | |
| 7,611,495 B1 | 11/2009 | Gianturco | |
| 7,651,475 B2 | 1/2010 | Angel | |
| 7,662,110 B2 | 2/2010 | Flaherty | |
| 7,664,545 B2 | 2/2010 | Westersten et al. | |
| 7,666,339 B2 | 2/2010 | Chaouk et al. | |
| D615,192 S | 5/2010 | Mudd et al. | |
| 7,722,582 B2 | 5/2010 | Lina et al. | |
| 7,762,983 B2 | 7/2010 | Arnissolle | |
| 7,850,656 B2 | 12/2010 | McKay et al. | |
| 7,850,683 B2 | 12/2010 | Elkins | |
| 7,878,981 B2 | 2/2011 | Strother et al. | |
| 7,896,837 B2 | 3/2011 | Wilkinson et al. | |
| D637,287 S | 5/2011 | Mudd et al. | |
| 7,998,170 B2 | 8/2011 | Cunningham | |

(56) References Cited

U.S. PATENT DOCUMENTS

| | | |
|---|---|---|
| 8,012,139 B2 | 9/2011 | McKay et al. |
| 8,029,460 B2 | 10/2011 | Rush et al. |
| 8,066,629 B2 | 11/2011 | Dlugos |
| 8,083,722 B2 | 12/2011 | McKay et al. |
| 8,088,108 B2 | 1/2012 | Kraft |
| 8,157,830 B2 | 4/2012 | Wenchell |
| 8,172,815 B2 | 5/2012 | Down et al. |
| 8,216,190 B2 | 7/2012 | Gartstein |
| 8,236,021 B2 | 8/2012 | Kluge |
| 8,291,768 B2 | 10/2012 | Spiegel |
| 8,303,518 B2 | 11/2012 | Aceti |
| 8,303,545 B2 | 11/2012 | Schraga |
| 8,343,132 B2 | 1/2013 | Heneveld et al. |
| 8,349,554 B2 | 1/2013 | Bahrami et al. |
| 8,353,871 B2 | 1/2013 | Zimmerman |
| 8,357,795 B2 | 1/2013 | Lebreton |
| 8,366,643 B2 | 2/2013 | Deem |
| 8,394,118 B2 | 3/2013 | Jones et al. |
| 8,409,147 B2 | 4/2013 | Kraft |
| 8,409,185 B2 | 4/2013 | Burger |
| 8,480,630 B2 | 7/2013 | Mudd et al. |
| 8,535,278 B2 | 9/2013 | Mudd et al. |
| 8,562,571 B2 | 10/2013 | Mudd et al. |
| 8,603,028 B2 | 12/2013 | Mudd et al. |
| 8,632,501 B2 | 1/2014 | Kraft |
| 8,636,797 B2 | 1/2014 | Chitre et al. |
| 8,657,786 B2 | 2/2014 | Bahrami et al. |
| 8,668,675 B2 | 3/2014 | Chase |
| 8,708,965 B2 | 4/2014 | Boyden |
| 8,712,815 B1 | 4/2014 | Nichols et al. |
| 8,821,446 B2 | 9/2014 | Trautman |
| 8,900,181 B2 | 12/2014 | Knowlton |
| 8,900,186 B2 | 12/2014 | Pettis et al. |
| 8,945,060 B2 | 2/2015 | Bunch |
| 9,017,289 B2 | 4/2015 | Backes |
| 9,017,318 B2 | 4/2015 | Fourkas |
| 9,039,688 B2 | 5/2015 | Palmer, III |
| 9,066,712 B2 | 6/2015 | Fourkas |
| 9,072,498 B2 | 7/2015 | Elkins |
| 9,101,346 B2 | 8/2015 | Burger |
| 9,113,855 B2 | 8/2015 | Burger |
| 9,149,331 B2 | 10/2015 | Deem |
| 9,155,584 B2 | 10/2015 | Fourkas |
| 9,180,273 B2 | 11/2015 | Konstantino |
| 9,214,030 B2 | 12/2015 | Sole et al. |
| 9,227,023 B2 | 1/2016 | Kraft |
| 9,241,753 B2 | 1/2016 | Fourkas |
| 9,254,162 B2 | 2/2016 | Burger |
| 9,289,605 B2 | 3/2016 | Choi |
| 9,314,568 B2 | 4/2016 | Gurtner et al. |
| 9,468,748 B2 | 10/2016 | Bang |
| 10,232,129 B2 * | 3/2019 | Tezel ............... A61M 5/347 |
| 2001/0008937 A1 | 7/2001 | Callegaro et al. |
| 2002/0010433 A1 * | 1/2002 | Johnson ............ A61M 5/347 |
| | | 604/241 |
| 2002/0026039 A1 | 2/2002 | Bellini et al. |
| 2002/0065483 A1 | 5/2002 | Leon |
| 2002/0133114 A1 | 9/2002 | Itoh |
| 2002/0151843 A1 | 10/2002 | Correa et al. |
| 2003/0028154 A1 | 2/2003 | Ros |
| 2003/0050602 A1 | 3/2003 | Pettis et al. |
| 2003/0078912 A1 | 4/2003 | Oliver |
| 2003/0144632 A1 | 7/2003 | Hommann et al. |
| 2003/0181863 A1 | 9/2003 | Ackley |
| 2003/0199883 A1 | 10/2003 | Laks |
| 2004/0010224 A1 | 1/2004 | Bodmeier |
| 2004/0015133 A1 | 1/2004 | Karim |
| 2004/0092927 A1 | 5/2004 | Podhajsky et al. |
| 2004/0122377 A1 | 6/2004 | Fischer et al. |
| 2004/0147883 A1 | 7/2004 | Tsai |
| 2004/0192643 A1 | 9/2004 | Pressato et al. |
| 2004/0220532 A1 * | 11/2004 | Caizza ............... A61M 5/346 |
| | | 604/905 |
| 2005/0033362 A1 | 2/2005 | Grafton |
| 2005/0085767 A1 | 4/2005 | Menassa |
| 2005/0131353 A1 | 6/2005 | Mossanen-Shams et al. |
| 2005/0137496 A1 | 6/2005 | Walsh et al. |
| 2005/0177117 A1 | 8/2005 | Crocker et al. |
| 2005/0182446 A1 | 8/2005 | DeSantis |
| 2005/0215956 A1 | 9/2005 | Nerney |
| 2005/0261633 A1 | 11/2005 | Khalaj |
| 2006/0041320 A1 | 2/2006 | Matsuda |
| 2006/0079765 A1 | 4/2006 | Neer |
| 2006/0089594 A1 | 4/2006 | Landau |
| 2006/0150742 A1 | 7/2006 | Esnouf |
| 2007/0038181 A1 | 2/2007 | Melamud |
| 2007/0083155 A1 | 4/2007 | Muller |
| 2007/0085767 A1 | 4/2007 | Jung et al. |
| 2007/0100363 A1 | 5/2007 | Dollar et al. |
| 2007/0167920 A1 | 7/2007 | Hommann |
| 2007/0212385 A1 | 9/2007 | David |
| 2007/0250010 A1 | 10/2007 | Hohlfelder et al. |
| 2007/0270710 A1 | 11/2007 | Frass et al. |
| 2008/0015522 A1 | 1/2008 | Yeshurun |
| 2008/0033347 A1 | 2/2008 | D'Arrigo et al. |
| 2008/0058706 A1 | 3/2008 | Zhang |
| 2008/0058839 A1 | 3/2008 | Nobles |
| 2008/0071385 A1 | 3/2008 | Binette et al. |
| 2008/0097325 A1 | 4/2008 | Tanaka et al. |
| 2008/0108952 A1 | 5/2008 | Horvath et al. |
| 2008/0114305 A1 | 5/2008 | Gerondale |
| 2008/0119797 A1 | 5/2008 | Kim |
| 2008/0119876 A1 | 5/2008 | Price et al. |
| 2008/0161772 A1 | 7/2008 | Nayak |
| 2008/0167674 A1 | 7/2008 | Bodduluri et al. |
| 2008/0188816 A1 | 8/2008 | Shimazaki |
| 2008/0200758 A1 | 8/2008 | Orbay et al. |
| 2008/0281278 A1 | 11/2008 | Williams |
| 2008/0284167 A1 | 11/2008 | Lim et al. |
| 2009/0088703 A1 * | 4/2009 | Azar ................ A61M 35/003 |
| | | 604/246 |
| 2009/0124996 A1 | 5/2009 | Heneveld et al. |
| 2009/0125050 A1 | 5/2009 | Dixon |
| 2009/0143746 A1 | 6/2009 | Mudd et al. |
| 2009/0187118 A1 | 7/2009 | Kim |
| 2009/0234322 A1 | 9/2009 | Fischer |
| 2009/0240200 A1 | 9/2009 | Heneveld et al. |
| 2009/0247953 A1 | 10/2009 | Yeshurun |
| 2009/0259180 A1 | 10/2009 | Choi |
| 2009/0275917 A1 | 11/2009 | Azar |
| 2009/0287161 A1 | 11/2009 | Traub |
| 2009/0299328 A1 | 12/2009 | Mudd et al. |
| 2010/0006095 A1 | 1/2010 | Woodcock |
| 2010/0030152 A1 | 2/2010 | Lee et al. |
| 2010/0069848 A1 | 3/2010 | Alferness |
| 2010/0100114 A1 | 4/2010 | Berger |
| 2010/0121307 A1 | 5/2010 | Lockard |
| 2010/0152675 A1 | 6/2010 | McClintock |
| 2010/0152679 A1 | 6/2010 | Tezel |
| 2010/0179488 A1 | 7/2010 | Spiegel |
| 2010/0256594 A1 | 10/2010 | Kimmell |
| 2010/0256596 A1 | 10/2010 | Chomas |
| 2010/0280488 A1 | 11/2010 | Pruitt et al. |
| 2010/0282774 A1 | 11/2010 | Greter et al. |
| 2010/0286618 A1 | 11/2010 | Choi |
| 2011/0009808 A1 | 1/2011 | AlGhamdi |
| 2011/0021905 A1 | 1/2011 | Patrick et al. |
| 2011/0028910 A1 | 2/2011 | Weber |
| 2011/0092916 A1 | 4/2011 | Tezel et al. |
| 2011/0137286 A1 | 6/2011 | Mudd et al. |
| 2011/0152926 A1 | 6/2011 | Vetrecin |
| 2011/0160674 A1 | 6/2011 | Holmes et al. |
| 2011/0172645 A1 | 7/2011 | Moga |
| 2011/0190974 A1 | 8/2011 | Holmes et al. |
| 2011/0202014 A1 | 8/2011 | Mutzbauer |
| 2011/0218494 A1 | 9/2011 | Assaf |
| 2011/0218497 A1 | 9/2011 | Assaf |
| 2011/0230839 A1 | 9/2011 | Bahrami et al. |
| 2011/0238038 A1 | 9/2011 | Sefi |
| 2011/0263724 A1 | 10/2011 | Gurtner |
| 2011/0319865 A1 | 12/2011 | Buss |
| 2012/0041374 A1 | 2/2012 | Lee |
| 2012/0089211 A1 | 4/2012 | Curtis |
| 2012/0101475 A1 | 4/2012 | Wilmot |

(56) References Cited

U.S. PATENT DOCUMENTS

| | | |
|---|---|---|
| 2012/0123194 A1 | 5/2012 | Beckman |
| 2012/0123537 A1 | 5/2012 | Manesis et al. |
| 2012/0141532 A1 | 6/2012 | Blanda et al. |
| 2012/0150266 A1 | 6/2012 | Shalev |
| 2012/0245629 A1 | 9/2012 | Gross et al. |
| 2012/0259322 A1 | 10/2012 | Fourkas |
| 2012/0265064 A1 | 10/2012 | Bahrami et al. |
| 2012/0265171 A1 | 10/2012 | Thorne |
| 2012/0296206 A1 | 11/2012 | Bahrami et al. |
| 2013/0012865 A1 | 1/2013 | Sallberg et al. |
| 2013/0041346 A1 | 2/2013 | Alon |
| 2013/0096531 A1 | 4/2013 | Estepa et al. |
| 2013/0122068 A1 | 5/2013 | Fermanian et al. |
| 2013/0131632 A1 | 5/2013 | Mudd et al. |
| 2013/0131633 A1 | 5/2013 | Mudd et al. |
| 2013/0150826 A1 | 6/2013 | Almohizea |
| 2013/0184648 A1 | 7/2013 | Inou et al. |
| 2013/0184696 A1 | 7/2013 | Fourkas |
| 2013/0197446 A1 | 8/2013 | Gustafsson |
| 2013/0197449 A1 | 8/2013 | Franklin et al. |
| 2013/0211374 A1 | 8/2013 | Hetherington |
| 2013/0253289 A1 | 9/2013 | Hadvary |
| 2013/0274655 A1 | 10/2013 | Jennings |
| 2013/0274670 A1 | 10/2013 | Mudd et al. |
| 2013/0280755 A1 | 10/2013 | Hubert |
| 2013/0310763 A1 | 11/2013 | Mudd et al. |
| 2013/0345587 A1 | 12/2013 | Colman |
| 2014/0018770 A1 | 1/2014 | Sutkin |
| 2014/0018835 A1 | 1/2014 | Scherkowski |
| 2014/0066845 A1 | 3/2014 | Mudd et al. |
| 2014/0088502 A1 | 3/2014 | Matheny et al. |
| 2014/0088553 A1 | 3/2014 | Hetherington |
| 2014/0114279 A1 | 4/2014 | Klinghoffer |
| 2014/0121587 A1 | 5/2014 | Sallberg et al. |
| 2014/0128685 A1 | 5/2014 | Na |
| 2014/0128810 A1 | 5/2014 | Ozawa et al. |
| 2014/0162901 A1 | 6/2014 | Bahrami et al. |
| 2014/0170299 A1 | 6/2014 | Gill |
| 2014/0228950 A1 | 8/2014 | Whitcup et al. |
| 2014/0228971 A1 | 8/2014 | Kim |
| 2014/0249504 A1 | 9/2014 | Franklin et al. |
| 2014/0257190 A1 | 9/2014 | Yue et al. |
| 2014/0309590 A1 | 10/2014 | Bahrami et al. |
| 2014/0343481 A1 | 11/2014 | Ignon |
| 2014/0350514 A1 | 11/2014 | Levin |
| 2014/0350516 A1 | 11/2014 | Schwab |
| 2014/0350517 A1 | 11/2014 | Dominguez |
| 2014/0350518 A1 | 11/2014 | Franklin et al. |
| 2014/0350536 A1 | 11/2014 | Allison |
| 2015/0025459 A1 | 1/2015 | Kimmel |
| 2015/0025563 A1 | 1/2015 | Mosharrafa et al. |
| 2015/0119875 A1 | 4/2015 | Fischell et al. |
| 2015/0126929 A1 | 5/2015 | Franklin et al. |
| 2015/0141956 A1 | 5/2015 | Hoffman et al. |
| 2015/0157809 A1 | 6/2015 | Park et al. |
| 2015/0209265 A1 | 7/2015 | Horne |
| 2015/0343147 A1 | 12/2015 | Franklin et al. |
| 2016/0007990 A1 | 1/2016 | Solish et al. |
| 2016/0058488 A1 | 3/2016 | Fourkas |
| 2016/0095984 A1 | 4/2016 | Franklin et al. |
| 2016/0114144 A1 | 4/2016 | Sumida |
| 2016/0144125 A1 | 5/2016 | Franklin |
| 2016/0207253 A9 | 7/2016 | Down et al. |
| 2016/0213854 A1 | 7/2016 | Schwab et al. |
| 2016/0263358 A1 | 9/2016 | Unger |
| 2016/0303314 A1 | 10/2016 | Momose |
| 2017/0080154 A1 | 3/2017 | Mudd et al. |
| 2017/0290987 A1 | 10/2017 | Mandaroux et al. |

FOREIGN PATENT DOCUMENTS

| | | |
|---|---|---|
| CN | 200960353 | 10/2007 |
| EP | 0362484 | 4/1990 |
| EP | 0205915 | 7/1990 |
| EP | 0167662 | 12/1990 |
| EP | 0648474 | 4/1995 |
| EP | 0809968 | 12/1997 |
| EP | 0838229 | 4/1998 |
| EP | 1051988 | 11/2000 |
| EP | 1332768 | 8/2003 |
| EP | 1486218 | 12/2004 |
| EP | 1395320 | 6/2006 |
| EP | 1859827 | 11/2007 |
| EP | 1923086 | 5/2008 |
| EP | 2189173 | 5/2010 |
| EP | 2335755 | 6/2011 |
| EP | 2422832 | 2/2012 |
| EP | 2103262 | 2/2013 |
| EP | 2184016 | 4/2013 |
| EP | 2671516 | 12/2013 |
| FR | 53011 | 9/1945 |
| FR | 2622457 | 5/1989 |
| FR | 2857654 | 1/2005 |
| GB | 2336783 | 5/2003 |
| IN | 209387 | 9/2007 |
| KR | 20120007473 | 1/2012 |
| KR | 101246570 | 3/2013 |
| KR | 20130036921 | 4/2013 |
| KR | 20130130436 | 12/2013 |
| KR | 20130132196 | 12/2013 |
| KR | 20140029007 | 3/2014 |
| RU | 2286803 | 11/2006 |
| WO | WO 90/001349 | 2/1990 |
| WO | WO 92/013579 | 8/1992 |
| WO | WO 94/012228 | 6/1994 |
| WO | WO 96/025965 | 8/1996 |
| WO | WO 97/028840 | 8/1997 |
| WO | WO 99/048601 | 9/1999 |
| WO | WO 01/00190 | 1/2001 |
| WO | WO 02/055135 | 7/2002 |
| WO | WO 2004/022603 | 3/2004 |
| WO | WO 2005/095225 | 10/2005 |
| WO | WO 2005/112888 | 12/2005 |
| WO | WO 2006/065837 | 6/2006 |
| WO | WO 2008/086479 | 8/2006 |
| WO | WO 2006/118804 | 11/2006 |
| WO | WO 2006/133111 | 12/2006 |
| WO | WO 2007/092929 | 8/2007 |
| WO | WO 2007/140381 | 12/2007 |
| WO | WO 2008/019265 | 2/2008 |
| WO | WO 2008/053481 | 5/2008 |
| WO | WO 2008/072229 | 6/2008 |
| WO | WO 2008/079824 | 7/2008 |
| WO | WO 2008/148071 | 12/2008 |
| WO | WO 2009/003135 | 12/2008 |
| WO | WO 2009/035680 | 3/2009 |
| WO | WO 2009/091099 | 7/2009 |
| WO | WO 2009/098666 | 8/2009 |
| WO | WO 2009/158145 | 12/2009 |
| WO | WO 2010/015901 | 2/2010 |
| WO | WO 2010/028025 | 3/2010 |
| WO | WO 2011/016785 | 2/2011 |
| WO | WO 2011/073796 | 6/2011 |
| WO | WO 2011/075731 | 6/2011 |
| WO | WO 2011/109129 | 9/2011 |
| WO | WO 2011/109130 | 9/2011 |
| WO | WO 2012/054301 | 4/2012 |
| WO | WO 2012/054311 | 4/2012 |
| WO | WO 2012/127856 | 9/2012 |
| WO | WO 2012/172424 | 12/2012 |
| WO | WO 2013/005881 | 1/2013 |
| WO | WO 2013/054165 | 4/2013 |
| WO | WO 2013/055832 | 4/2013 |
| WO | WO 2013/082112 | 6/2013 |
| WO | WO 2013/106857 | 8/2013 |
| WO | WO 2014/026044 | 2/2014 |
| WO | WO 2014/034032 | 3/2014 |
| WO | WO 2012/174464 | 5/2014 |
| WO | WO 2014/064536 | 5/2014 |
| WO | WO 2014/189161 | 11/2014 |
| WO | WO 2015/007243 | 1/2015 |
| WO | WO 2015/020982 | 2/2015 |
| WO | WO 2013/065235 | 4/2015 |
| WO | WO 2015/064031 | 5/2015 |

(56) References Cited

FOREIGN PATENT DOCUMENTS

| WO | WO 2015/105269 | 7/2015 |
|---|---|---|
| WO | WO 2015/127339 | 8/2015 |
| WO | WO 2015/149031 | 10/2015 |
| WO | WO 2016/008845 | 1/2016 |
| WO | WO 2016/022865 | 2/2016 |
| WO | WO 2016/033584 | 3/2016 |
| WO | WO 2016/033586 | 3/2016 |

OTHER PUBLICATIONS

U.S. Appl. No. 61/085,956, filed Aug. 4, 2008.
U.S. Appl. No. 12/393,884, filed Feb. 26, 2009 (now U.S. Pat. No. 8,357,795).
Haake RheoStress 600, Brochure/Data Sheet, 2003, 6 pages.
Thermo Haake Focus, Issue 5, Apr. 2002, 6 pages.
Falcone et al., "Crosslinked hyaluronic acid dermal fillers: a comparison of rheological properties," 2008, Journal of Biomedical Materials Research, vol. 87 Part A, pp. 264-271.
Parker, McGraw-Hill Encyclopedia of Engineering, 1993, Ed 2, definition of "threading".
Collocott et al., Dictionary of Science and Technology, 1942, definition of "screw thread".
Brockhaus ABC Naturwissenschaft und Technik A-K, 1980, 3 pages.
EP 2384210 Response to Opponent's Submission dated Oct. 8, 2019, 8 pages.
EP 2384210 Merz Reply to Proprietor's Submission, Oct. 16, 2019, 5 pages.
EP 3187219—Third Party Observations dated Feb. 4, 2020, 34 pages.
Smith, "Practical User of Juvederm: Early Experience," Plast. Reconstr. Surg, Nov. 2007, pp. 67S-73S.
Summary of Safety and Effectiveness Data—Juvederm—Premarket Approval Application No. P050047, Jun. 2, 2006, 19 pages.
EP 2384210—Third Party Observations dated Mar. 17, 2020, 32 pages.
Carruthers, et al., "Soft Tissue Augmentation," 2$^{nd}$ Edition, 2008 Elsevier Inc., 28 pages.
FDA approval information about Juvederm 24HV and Juvederm 30HV, downloaded Nov. 3, 2020 from https://www.accessdata.fda.gov/scripts/cdrh/devicesatfda/index.cfm, 73 pages.
FDA approval information about Restylane injectable gel, downloaded Nov. 3, 2020 from https://www.accessdata.fda.gov/scripts/cdrh/devicesatfda/index.cfm?db=pma&id=320211, 31 pages.
Forwarding of Submissions to Parties from European Patent No. 2384210, dated Oct. 5, 2021, 32 pages.
Preliminary Non-binding Opinion of the Opposition Division from European Patent No. 3187219, dated Oct. 29, 2021, 18 pages.
Bleyer, "SIS Facial Implant 510(k) Summary," Cook Biotech Inc. May 2005.
Davidenko et al., "Collagen-hyaluronic acid scaffolds for adipose tissue engineering", ACTA Biomaterialia, vol. 6, No. 10, Oct. 1, 2010, pp. 3957-3968.
Galderma, "New Restylane Skinboosters SmartClick delivery system wins prestigious Red Dot design award," Jul. 4, 2014, retrieved from http://www.galderma.com/News/articleType/ArticleView/articleId/64/New-Restylane-Skinboosters-SmartClick-delivery-system-wins-prestigious-Red-Dot-design-award.
Galderma, "Restylane Smart Click System Injection Device," Mar. 2015, retrieved from http://www.red-dot-21.com/products/restylane-smart-click-system-injection-device-22169.
Hamza et al., "A new external filling device in tissue expansion," Plastic and Reconstructive Surgery, Mar. 1998, vol. 101, No. 3, pp. 813-815.
Indian Patent Application No. 190/CHE/2002, filed Mar. 20, 2002, entitled A Subcutaneous Tissue Expander.
Indian Patent Application No. IN2012KO01267 for Tissue Expander.
International Search Report from PCT/US2016/021838, dated May 17, 2016.
International Search Report and Written Opinion from PCT/US2009/045831, dated Feb. 24, 2010.
International Search Report and Written Opinion from PCT/US2014/039265.
International Search Report and Written Opinion from PCT/US2014/039266.
Park et al., "Biological characterization of EDC-crosslinked collagen-hyaluronic acid matrix in dermal tissue restoration", Biomaterials, Elsevier Science Publishers BV, vol. 24, No. 9, Apr. 1, 2003, pp. 1631-1641.
PRIME Journal, "Galderma to launch two new syringes at AMWC 2014," Mar. 2014.
Turtlepin, "The Painless Direct Dermal Injector" Product Information, JM Biotech Co Ltd, 2013.
Wang et al., "In vivo stimulation of de novo collagen production caused by cross-linked hyaluronic acid dermal filler injections in photodamaged human skin.", Archives of Dermatology, American Medical Association, US, vol. 143, No. 2, Feb. 1, 2007, pp. 155-163.
Summary and Safety and Effectiveness Data (FDA approval information about PERLANE injectable gel) May 2, 2007, 16 pages.
"What is an ISO 80369-7 compliant Luer?—The New Luer Standard" retrieved from www.industrialspec.com/about-us/blog/detail/what-are-iso-80369-7-compliant-luers, Jun. 15, 2021, 8 pages.
Brief Communication—Response to the preliminary opinion of the Opposition Division annexed to the Summons to attend oral proceedings dated Oct. 29, 2021, from European Patent No. 3187219, dated Apr. 29, 2022, 22 pages.
Baumann, Leslie, and Marianna L. Blyumin. "Update on Dermal Filling Agents: The University of Miami Department of Dermatology's Cosmetic Center Perspective." Cosmetic Dermatology—Cedar Knolls—21.5 (2008): 268-278.
"Basics of rheology," retrieved from https://wiki.anton-paar.com/en/basics-of-rheology, 23 pages.
German Standard EN 1707, Jan. 1997, 12 pages plus one page summary.
German Standard EN 20 594-1, Jan. 1995, 10 pages plus one page summary.
German Standard EN ISO 7864, Jan. 1996, 11 pages plus one page summary.
German Standard EN ISO 7886-1, Oct. 1997, 21 pages plus one page summary.
EP 09764680.6—Brief Communication—Letter from the Opponent dated Aug. 16, 2019, 29 pages.
EP 09764680.6—Summons to Attend Oral Proceedings dated Feb. 20, 2019, 11 pages.

* cited by examiner

INJECTION DEVICE

RELATED APPLICATIONS

This application is a continuation of U.S. patent application Ser. No. 12/629,480, filed on Dec. 2, 2009, which claims the benefit of U.S. Provisional Patent Application No. 61/119,298, filed on Dec. 2, 2008 and U.S. Provisional Patent Application No. 61/139,430, filed on Dec. 19, 2008, the entire disclosure of each of which is incorporated herein by this specific reference.

BACKGROUND

The present invention is generally directed to non-surgical devices for the correction of skin contour defects and aging and is more particularly directed to an injection device for enabling introduction of a dermal filler into peripheral locations of a human body through a cannula.

Dermal fillers such as, such as Juvederm™, a hyaluronic acid based formulation, have been used for the treatment of nasal labial folds, lip augmentation, tear troughs, and for facial volumizing through the use of very fine syringe needles.

The dermal fillers are of high viscosity and this provides for effective, and preferably substantially uniform, suspension of the dermal filler into a peripheral location.

A relatively small needle size, gauge, is preferred for delivery of the dermal filler in order to lessen complications and recovery time. However, in combination with the relatively high viscosity of the dermal filler, a problem can arise with regard to needle assembly separation from the syringe due to the high pressure generated by a piston reacting on the high viscosity dermal filler in order to eject the filler from the syringe through a fine needle and into the patient.

The present invention overcomes this problem by providing an ejection device which eliminates, or substantially reduces, the probability of needle assembly/syringe separation during a procedure.

SUMMARY OF THE INVENTION

An injection device in accordance with the present invention generally includes a syringe having a body with a piston disposed therein and an open distal end.

A needle assembly is provided which includes a cannula and a luer connector engagable with the syringe distal end. The needle or cannula, hereinafter "cannula", has a gauge of about 18 to a gauge of about 25 or greater. The luer connector includes a hub with a distal end supporting the cannula and a proximal end matable with the syringe distal end.

In one embodiment, the present invention further includes a viscous fluid, for example, a hyaluronic acid-based dermal filler, disposed in the syringe's body and which is injectable by the piston into a peripheral location of a human or animal body through the cannula.

The mating engagement, for example, between the hub and the syringe distal end is provided by internal threads disposed in the syringe distal end and external threads disposed on the hub, as well as between a tapered syringe cone and a tapered inside surface of the hub. The internal threads have a pitch which is sufficient to prevent detachment of the hub from syringe distal end during injection of the viscous fluid into a peripheral location of a human or animal body.

More particularly, in one embodiment, the internal threads have a pitch of between about 2 mm and about 5 mm. For example, the internal threads have a pitch of about 3 mm. The internal thread may be double lead screw threads. In addition, the external threads disposed on the hub further may also be double lead screw threads and the double lead screw threads provide an advantage of enabling the hub to travel twice the distance into mating engagement with the syringe distal end with each single turn of the hub. In other embodiments, the internal threads have a pitch of about 2.0 mm, about 3.0 mm, about 3.5 mm, about 4 mm, about 4.5 mm or about 5 mm. In addition, the external threads may have a pitch of about 2.0 mm, about 3.0 mm, about 3.5 mm, about 4 mm, about 4.5 mm or about 5 mm.

In a specific embodiment, the external threads comprise single circumference double lead screw threads as will be hereinafter described in greater detail.

In addition, a cavity, for example, a stepped cavity, is disposed in the hub. The cavity serves not only reduces dead space in the syringe but also significantly reduces the possibility of detachment of the hub from the syringe distal end during operation of the piston to eject the viscous fluid through the cannula. Thus, the cavity can be considered a hub retention cavity.

BRIEF DESCRIPTION OF THE DRAWINGS

The advantages and features of the present invention will be better understood by the following description when considered in conjunction with the accompanying drawings in which.

DETAILED DESCRIPTION

Figures 1, 2, 3, 4:
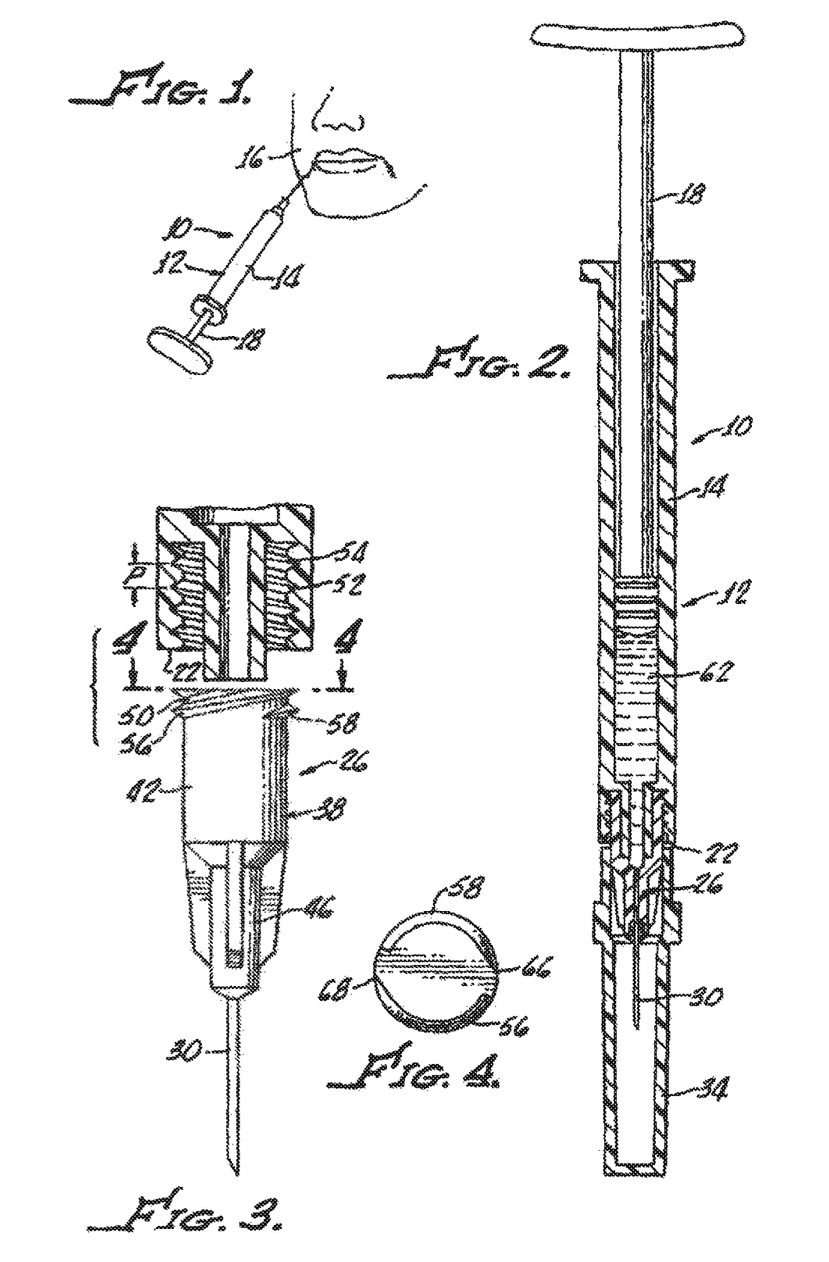
FIG. 1 is an illustration of use of an injection device in accordance with the present invention for injecting a viscous fluid into a peripheral location of the human, generally showing a syringe having a body with a piston and a needle assembly.
FIG. 2 is a cross sectional view of the syringe shown in FIG. 1 illustrating more clearly showing the syringe body along with a needle assembly with a luer connector engagable with a distal end of the syringe along with a viscous fluid disposed in the syringe body.
FIG. 3 is an enlarged cross sectional view of the mating engagement between a luer connector hub and a distal end of the syringe specifically illustrating internal threads disposed in the syringe distal end and external threads along the hub for enabling the mating engagement, along with a cavity disposed in the hub configured as a hub retention cavity.
FIG. 4 is end view of the hub illustrating double lead screws.

With reference to FIG. 1, there is shown an injection device 10 in accordance with the present invention having a syringe 12 with a body 14 with a piston 18 disposed therein.

With additional reference to FIGS. 2 and 3, the syringe 14 includes an open distal end 22, and a needle assembly 26. The needle assembly includes a cannula 30 along with a sheath 34 and a luer connector 38 engagable with the syringe open distal end 22, which includes a hub 42 having a distal end 46 and a proximal end 50 matable with the syringe distal end 22.

Internal threads 52, 54 and external threads 56, 58 enable the mating engagement. Pitch (P) of the threads 52, 54 enables the ejection of viscous fluid 62 through the cannula 30 upon operation of the piston 18 without separation of the hub 42 from the syringe open distal end 22 during ejection of the viscous fluid 62 as illustrated in FIG. 1.

In some embodiments, the viscous fluid 62 is a dermal filler. In some embodiments, the viscous fluid is a hyaluronic acid-based fluid having a viscosity between about 50,000 cps and about 500,000 cps, measured at about 25° C. with a controlled stress rheometer (RS600 TA Instrument) and a cone plate geometry (40 mm, 2°). In some embodiments, the viscous fluid is a hyaluronic acid based dermal filler having a viscosity greater than about 130,000 cps.

When measured with a traction column test (Versatest, Mecmesin), at 13 mm/min (extrusion speed) and a needle with a gauge between 21G to 32G, the viscous fluid may have an extrusion force of between about 5N up to about 200N, more specifically, an extrusion force of between about 10N to about 150N.

In an exemplary embodiment, the pitch of the hub threads 52, 54 is between about 2 mm and about 5 mm. Preferably, the pitch is about 3 mm. The threads 52, 54 and 56, 58 are preferably at least double lead screw threads, although triple, and even quadruple lead threads may used. As most clearly shown in FIG. 4, in one particular embodiment, the threads 52, 54 have two thread starts 66, 68 at a 180° radial displacement from one another.

As hereinabove noted, this enables rapid engagement of the hub 42 with the syringe open distal end 22.

In one embodiment, the hub 42 is formed from a low elasticity material, for example, an acrylic or a polycarbonate, rather than polypropylene typically used for syringe hubs, as hereinafter described in connection with needle retention tests. This further enhances the prevention of detachment of the hub 46 from the syringe open distal end 22.

Figure 5:
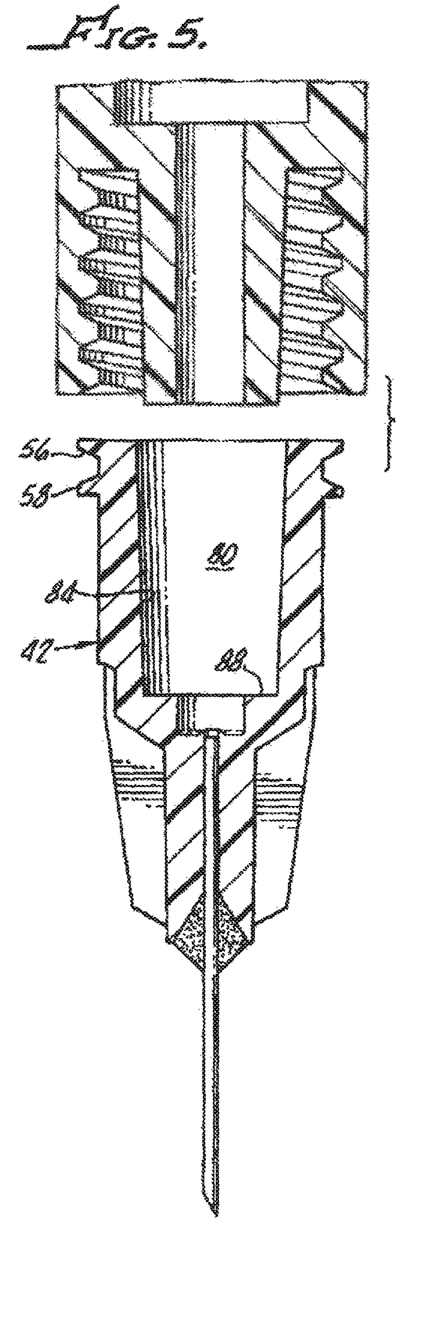
FIG. 5 is an enlarged cross section view of the needle assembly and an open distal end of the syringe body showing a tapered syringe cone engageable with a tapered inside surface of the needle assembly hub.
Figure 6:
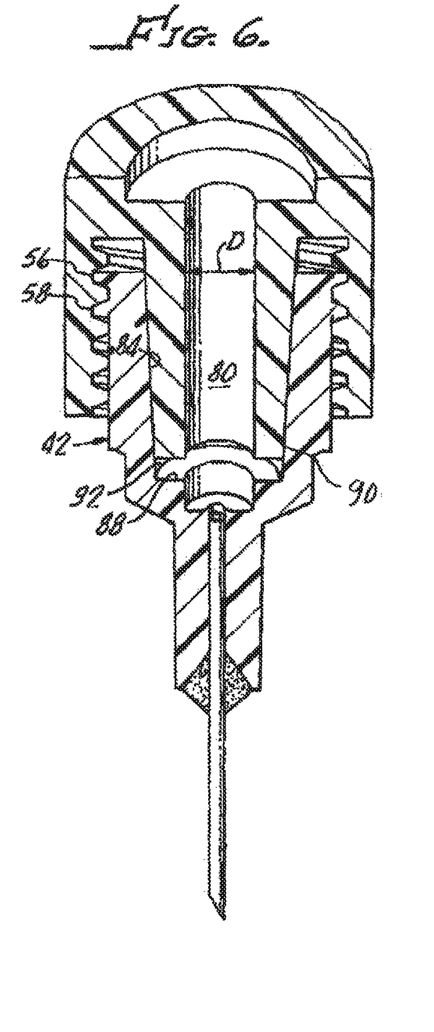
FIG. 6 is a cross-section view of the needle assembly engaged with the syringe's open distal end.

With reference to FIGS. 5 and 6, hub 42 includes a hub retention cavity 80 defined by an inside surface 84 of the hub 42 and a step 88, thus providing a unique stepped interior surface. When torqued to the syringe and maximally seated as shown in FIG. 6, a tapered syringe cone 90 stops short of the step 88 and creates a dead space 92 which is reduced by the step 88. Engagement between the cone 90 and inside surface 84, which is also tapered, provides a seal therebetween. Low dead space reduces the amount of fluid that cannot be administered. This is important in that the fluids to be administered, by injection, often are very expensive.

The step 88 unexpectedly prevents or substantially reduces the possibility of detachment of the hub 42 from the syringe cone 90 and syringe open distal end 22 during injection of the viscous fluid 62.

That is, the average detachment force is significantly greater with the step 88 formed in the cavity hub retention cavity 80 of the hub 42 as was discovered during comparison study as follows:

Test methods used in this study utilized equipment designed by Omnica Corporation specifically for torque setting and detachment testing.

The torque set unit utilizes a numerically controlled motor and torque sensor which tightens the needle hub 42 onto the syringe open distal end 22 and a pre-determined torque setting testing is shown that the static friction between the needle hub 42 and the syringe open distal end 22 materials causes more overshoot than observed with standard polypropylene hubs (not shown).

A detachment tester utilizes a numerically controlled motor driving linear carriage against a forced transducer.

In a comparison test, all of the hubs (not shown) were attached to the syringe open distal end 22 and cone 90 with a torque of 0.07 Nm (Newton meter). All of the tests were performed on 0.8 cc syringes having identical dimensions, for example, syringe open distal end 22 having an entry diameter D (see FIG. 6), of about 4 mm.

The results are shown in Table 1 for nominal torque static test needle retention with various design attribute combinations.

Table 1 shows that the conventional polypropylene hub mated to a syringe with 5 mm threads has an average detachment force 46.1 N (Newton) when the hub is attached to the syringe with a force of 0.07 Nm.

TABLE 1

Nominal torque Static Test Needle Retention with Various Design Attribute Combinations

| Needle Design | Average Detachment Force (N)[1] @ 0.07 Nm |
|---|---|
| Conventional Polypropylene Hub, Syringe with 5 mm Threads | 46.1 |
| Conventional Polypropylene Hub, Syringe with 3 mm Threads | 56.2 |
| Polycarbonate Hub and Syringe with 5 mm Threads | 83.2 |
| Polycarbonate Hub and Syringe with 3 mm Threads | 96.0 |
| Polycarbonate Hub and Syringe with 3 mm Threads and Stepped Cavity | 200+ |

Slight improvement shown in the conventional polypropylene hub attached to the syringe body with 3 mm threads, and an average detachment force of about 56.2 N.

Utilizing polycarbonate instead of polypropylene for the hub 42 results in an average detachment force of 83.2 N with 5 mm threads utilized for attachment.

Combination of polycarbonate hub 42 with 3 mm threads without a step 88 results in a 96 N average detachment force.

Surprisingly, the detachment force for the hub 42 with 3 mm threads incorporating the dead space reducing step 88 results in an average detachment force of more than 200 N.

It is contemplated that other structures may be useful in reducing dead space in a manner effective to increase detachment force relative to conventional syringe/needle combinations. For example, it is contemplated that reduced dead space can be accomplished, within the scope of the present invention, by reducing an outer diameter of the syringe luer tip, increasing an inner diameter of the hub cavity, and/or other ways effective to increase the engagement length of the syringe tip and the hub.

EXAMPLE

A multi-center, double-blind, randomized parallel-controlled prospective comparison study was undertaken to test needle disengagement rates. This study tested needle disengagement rates of a Polycarbonate Hub and Syringe with 3 mm Threads and Stepped Cavity in accordance with the present invention (study device) in comparison to a conventional polypropylene hub and syringe with 5 mm threads (conventional device). Needles of each of the conventional devices and the study devices tested were all 30 G X½"

needles. The material injected for the study was Juvederm™ Ultra Injectable Gel (dermal filler).

There were up to 288 study participants. Each study participant underwent treatment for improving his or her bilateral nasolabial folds using 2 syringes of dermal filler packaged in either the conventional device or the study device.

The results demonstrated a significant difference in needle disengagement rates between the conventional device and the study device. No disengagements were reported for the study device. Between 3% and 7% of the needles of the conventional device unintentionally disengaged during injection.

Although there has been hereinabove described a specific injection device in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A needle assembly for delivering a dermal filler, the assembly comprising:
   a cannula; and
   a hub having an inner bore, the inner bore comprising a proximal retention section, a stepped section, and a cannula retention section, the proximal retention section being mateable with a syringe, the stepped section being smaller in diameter than the proximal retention section and being disposed intermediate the proximal retention section and the cannula retention section, the inner bore having a stepped section surface wherealong the inner bore decreases in diameter to a proximal end of a cannula retention surface of the cannula retention section, the inner bore not increasing in diameter from the proximal retention section to a distal end of the cannula retention section, the cannula retention section having a constant diameter, the cannula retention surface being mated against an outer surface of the cannula to secure the cannula within the cannula retention section;
   wherein the hub comprises an inside surface of the proximal retention section, the inside surface comprising a tapered wall and a step, the step extending normal to a longitudinal axis extending through the needle assembly, the step being configured to be spaced apart from a distal-most surface of a tapered syringe cone of a syringe in a distal direction when the hub and the tapered syringe cone are maximally seated thereby reducing dead space within the proximal retention section for preventing detachment of the hub from the tapered syringe cone during injection of a dermal filler contained in a body of the syringe;
   wherein the cannula is distal to the step, and wherein the step is positioned a distance from the cannula, and wherein the outer surface of the cannula is mated against the cannula retention surface from the proximal end of the cannula retention surface to a distal end of the hub.

2. The assembly of claim 1, wherein the hub comprises external threads for coupling with a syringe.

3. The assembly of claim 1, wherein the cannula has a gauge of greater than about 25 G.

4. The assembly of claim 1, wherein the cannula has a gauge between 21 G and 32 G.

5. The assembly of claim 1, wherein the cannula retention surface extends normal to the stepped section surface.

6. The assembly of claim 1, wherein the cannula retention surface extends continuously with the stepped section surface.

7. The assembly of claim 1, wherein the stepped section has a constant diameter.

8. The assembly of claim 1, wherein the hub further comprises a luer connector.

9. The assembly of claim 2, wherein the external threads comprise double lead screw threads.

10. The assembly of claim 2, wherein the external threads comprise double lead screw threads.

11. An injection device for facilitating delivery of a dermal filler, the device comprising the needle assembly of claim 1 and a syringe having (i) a body with a piston disposed therein and (ii) an open distal end portion, the hub of the needle assembly engageable with the open distal end portion of the syringe.

12. A needle assembly for an injection device for facilitating delivery of a dermal filler, the assembly consisting essentially of:
    a cannula; and
    a hub having an inner bore, the inner bore comprising a proximal retention section, a stepped section, and a cannula retention section, the stepped section being smaller in diameter than the proximal retention section and being disposed intermediate the proximal retention section and the cannula retention section, the inner bore having a stepped section surface wherealong the inner bore decreases in diameter to a proximal end of a cannula retention surface of the cannula retention section, the inner bore not increasing in diameter from the proximal retention section to a distal end of the cannula retention section, the cannula retention section having a constant diameter, the cannula retention surface being mated against an outer surface of the cannula to secure the cannula within the cannula retention section;
    wherein the hub comprises an inside surface of the proximal retention section, the inside surface comprising a tapered wall and a step, the step extending normal to a longitudinal axis extending through the needle assembly, the step being configured to be spaced apart from a distal-most surface of a tapered syringe cone of a syringe in a distal direction when the proximal retention section and a distal end portion of a syringe are coupled thereby reducing dead space within the inner bore for preventing detachment of the hub from the syringe during an injection procedure;
    wherein the cannula is distal to the step, and wherein the step is positioned a distance from the cannula, and wherein the outer surface of the cannula is mated against the cannula retention surface from the proximal end of the cannula retention surface to a distal end of the hub.

13. The assembly of claim 12, wherein the cannula retention surface extends normal to the stepped section surface.

14. The assembly of claim 12, wherein the cannula retention surface extends continuously with the stepped section surface.

15. The assembly of claim 12, wherein the stepped section has a constant diameter.

16. The assembly of claim 12, wherein the hub further comprises a luer connector.

\* \* \* \* \*